(12) United States Patent
Lee et al.

(10) Patent No.: US 7,842,471 B2
(45) Date of Patent: Nov. 30, 2010

(54) ULTRA SENSITIVE BIOSENSOR FOR DETECTING BIO-SIGNAL TRANSMITTERS, AND DETECTOR AND DETECTING METHOD USING THE SAME

(75) Inventors: Changjoon Justin Lee, Seoul (KR); Dong-Ho Woo, Seoul (KR)

(73) Assignee: Korea Institute of Science and Technology, Hawolgok-dong, Seongbuk-gu, Seoul (KR)

( * ) Notice: Subject to any disclaimer, the term of this patent is extended or adjusted under 35 U.S.C. 154(b) by 42 days.

(21) Appl. No.: 12/022,442

(22) Filed: Jan. 30, 2008

(65) Prior Publication Data
US 2009/0042234 A1 Feb. 12, 2009

(30) Foreign Application Priority Data
Aug. 7, 2007 (KR) ...................... 10-2007-0079073

(51) Int. Cl.
*G01N 33/53* (2006.01)
(52) U.S. Cl. ....................................................... 435/7.2
(58) Field of Classification Search ........................ None
See application file for complete search history.

(56) References Cited
U.S. PATENT DOCUMENTS
6,376,198 B1   4/2002   Kopin et al.

FOREIGN PATENT DOCUMENTS
KR   10-0560122   12/2005

OTHER PUBLICATIONS

Lee et al., J Physiol 581(3):1057-1081, 2007 (first published on-line Apr. 5, 2007).*
Pasti et al., Journal of Neuroscience, 21(2):477-484, 2001.*
Stern-Bach et al., Neuron, 21:907-918, 1998.*
Allen, T.G.J., Trends Neurosci., vol. 20, No. 5, pp. 192-197 (1997), The 'sniffer-patch' technique for detection of neurotransmitter release.

* cited by examiner

*Primary Examiner*—Marianne P Allen
(74) *Attorney, Agent, or Firm*—Lexyoume IP Group, PLLC.

(57) ABSTRACT

The present invention relates to a novel use of a transfected cell as a biosensor, wherein the transfected cell expresses a receptor specific to a bio-signal transmitter, and a highly sensitive detector and a highly sensitive detecting method of a bio-signal transmitter using the biosensor. The bio-signal transmitter detecting technique according to the present invention has an advantage of being applied to a sniffer-patch method, and is capable of providing millisecond time resolution for detecting nanomolar levels of the bio-signal transmitter to be detected.

5 Claims, 6 Drawing Sheets

ULTRA SENSITIVE BIOSENSOR FOR DETECTING BIO-SIGNAL TRANSMITTERS, AND DETECTOR AND DETECTING METHOD USING THE SAME

CROSS-REFERENCE TO RELATED APPLICATION

This application claims priority to and the benefit of Korean Patent Application No. 10-2007-0079073 filed in the Korean Intellectual Property Office on Aug. 7, 2007, the entire contents of which are incorporated herein by reference.

BACKGROUND OF THE INVENTION (a) Field of the Invention

The present invention relates to a novel use of a transfected cell as a biosensor, wherein the transfected cell expresses a receptor specific to a bio-signal transmitter, and a highly sensitive detector and a highly sensitive detecting method of a bio-signal transmitter using the biosensor.

(b) Description of the Related Art

Bio-signal transmitters generally refer to a series of materials including all kinds of hormones, neurotransmitters, and other intercellular signal transmitters that are released from many kinds of tissues or cells in the body and transmit information to adjacent tissues or cells. Of them, the neurotransmitters may be generally classified into four classes, i.e., an amino acid-based class (e.g., acetylcholine, glycine, aspartic acid, glutamate, and the like), an amine-based class (e.g., dopamine, adrenalin (epinephrine), noradrenalin, Gamma-aminobutyric acid (GABA), and the like), a peptide-based class (e.g., vasopressin, and the like.), and a fatty acid-based class (e.g., histamine, serotonin, and the like). It has been known that the above compounds are released into synapses and participate in transmitting information between neurons. Such neurotransmitter release plays an important role in neurotransmission between neurons, and a very small change of the released amount affects the neurotransmission. Nevertheless, since the released amount is extremely small, it has been difficult as well as important to achieve highly sensitive detection and quantification of the bio-signal transmitter release.

Although there has been much research into the development of techniques of detecting and measuring the bio-signal transmitter release from bio-samples, none of the research has been successful in developing techniques that simultaneously satisfy high sensitivity together with a higher time and spatial resolution required for quantifying the release from a single cell level. Up to the present, most of the developed techniques have technical limits in directly detecting the bio-signal transmitter release from each position of the neural membrane.

Of the developed techniques, electrochemical methods, such as amperometry and fast cyclic voltametry, are useful for fast and highly sensitive detection of a bio-signal transmitter at an isolated position where the released bio-signal transmitter is readily oxidized or reduced. However, these methods are limited in the number of bio-signal transmitters to be detected. In order to solve this problem, there have been several attempts to improve the number of bio-signal transmitters to be detected by enzymatically converting the bio-signal transmitters into easily oxidizable intermediates. However, the enzymatic conversion step is too slow to detect the release from a single cell level.

Recently, a sniffer-patch detecting technique has been developed as an alternative to the above techniques. The sniffer-patch method, which was firstly used for detecting a spontaneous release of Ach (acetylcholine) from a developing growth cone, can provide a highly sensitive biological detection system utilizing a high affinity of a ligand-gated ion channel to a natural bio-signal transmitter. This method is based on a concept of excising a small patch of membrane on which many receptors exist from a donor cell using an outside-out configuration of a patch-clamp recording method, and detecting the release position of the bio-signal transmitter using the excised patch. The first step of the detection is to excise a membrane patch from a donor cell. Thereafter, the excised patch is voltage-clamped to a potential in a range capable of providing an impulse sufficient for ion transfer through the channel to be detected while preventing activation of voltage-gated ion channels.

Since the sniffer-patch method uses a membrane of a proper donor cell as a biosensor, it is required to develop donor cells that are suitable for a biosensor in order to achieve higher detection efficiency.

SUMMARY OF THE INVENTION

An embodiment of the present invention provides a biosensor including a transfected cell that express various receptors and ion channels that are used in a bio-signal transmitter detection method, such as a sniffer-patch method, for achieving efficient detection.

Another embodiment of the present invention provides a detector and a detecting method for highly sensitive detection of bio-signal transmitters using the biosensor.

BRIEF DESCRIPTION OF THE DRAWINGS

FIGS. 5a and 5b show a calcium increment depending on treatment of TFLLR in astrocytes, under the condition of with or without treatment of 5,7-dichlorokynurenic acid (DCKA) in the presence of glutamate, and the inward current amplitude induced from NR1-1a/NR2A2D transfected HEK, wherein 5a shows the cases in which glutamate and DCKA are all treated (right panel), and in which only glutamate is treated (left panel), wherein in each case, the upper trace represents the calcium increment recorded from astrocytes, and the lower trace shows the inward current recorded from HEK293 cells; and 5b is a bar graph for summary of current traces of left and right panels of 5a.

DETAILED DESCRIPTION OF THE EMBODIMENTS

In the following detailed description, only certain exemplary embodiments of the present invention have been shown and described, simply by way of illustration.

As those skilled in the art would realize, the described embodiments may be modified in various ways, all without departing from the spirit or scope of the present invention.

Accordingly, the drawings and description are to be regarded as illustrative in nature and not restrictive.

Like reference numerals designate like elements throughout the specification.

In addition, unless explicitly described to the contrary, the word "comprise", and variations such as "comprises" or "comprising", will be understood to imply the inclusion of stated elements, but not the exclusion of any other elements.

The present invention relates to a novel use of a transfected cell as a biosensor, wherein the transfected cell expresses a receptor specific to a bio-signal transmitter, a highly sensitive detector, and a highly sensitive detecting method of bio-signal transmitter using the biosensor. The bio-signal transmitter detecting technique according to the present invention has an advantage of being applied to a sniffer-patch method and that is capable of providing millisecond time resolution for detecting nanomolar levels of the bio-signal transmitter to be detected.

Firstly, in an embodiment, the present invention provides a biosensor for detecting a bio-signal transmitter, including a transfected cell expressing a receptor specific to the bio-signal transmitter to be detected and an ion channel regulated by the receptor.

The bio-signal transmitter is a material to be detected, and may be any material that has specific receptor(s) and causes a current change through ion channel(s) controlled by the receptor(s) when it binds to the receptor(s), for example one or more selected from the group consisting hormones, neurotransmitters, intercellular signal transmitters, and the like. The hormone may be any material secreted from an endocrine organ and carrying out signal transmission to target organ cells, for example one or more selected from the group consisting of vasopressin, insulin, and the like. The neurotransmitter may be any material for signal transmission released from all nervous tissues including neurons and astrocytes, for example one or more selected from the group consisting of acetylcholine, glycine, aspartic acid, D-serine, glutamate, dopamine, enkephalin, adrenalin, epinephrine, noradrenalin, Gamma-aminobutyric acid (GABA), histamine, serotonin, brain-derived neurotrophic factor (BDNF), nerve growth factor (NGF), substance P, neuropeptide Y, epidermal growth factor (EGF), calcitonin-gene related peptide (CGRP), and the like. The intercellular signal transmitter may be one or more selected from the group consisting of ATP, epidermal growth factor (EGF), and the like. Of the bio-signal transmitters, macromolecules such as BDNF, NGF, substance P, neuropeptide Y, EGF, and the like have only been able to be analyzed by high speed liquid chromatography (HPLC), and it is impossible for them to be sensitively analyzed to the nanomolar or micromolar levels. However, the present invention allows highly sensitive and accurate detection with nanomolar or micromolar detection limits and millisecond time resolution, as well as a real-time detection, which has not been achieved by HPLC.

The receptor is specific to the bio-signal transmitter to be detected and non-desensitized. For example, when the bio-signal transmitter to be detected is glutamate, the receptor may be any glutamate receptor, and is preferably one or more selected from the group consisting of GluR1, GluR1LY, GluR2, GluR3, GluR4, NR1/NR2A, NR1/NR2B, NR1/NR2c, NR1/NR2D, GluR5, GluR6, GluR7, mGluR1-7, and the like. In addition, when the bio-signal transmitter is ATP, the receptor may be P2X2; when the bio-signal transmitter is D-serine, the receptor may be NR1-1a/NR2A2D; when the bio-signal transmitter is GABA, the receptor may be GABAc; when the bio-signal transmitter is acetylcholine, the receptor may be a nicotinic receptor subunit; when the bio-signal transmitter is insulin, the receptor may be a insulin receptor; when the bio-signal transmitter is enkephalin, the receptor may be mu/GIRK; when the bio-signal transmitter is BDNF, the receptor may be TrkB/TRPC6; and when the bio-signal transmitter is NGF, the receptor may be TrkA/TRPC6. The bio-signal transmitter and the receptor corresponding thereto are well known in the relevant art, and once the bio-signal transmitter to be detected is settled, one skilled in the art may easily select the receptor corresponding to the bio-signal transmitter.

In the biosensor of the present invention, the host cell to be used for preparing the transfected cell expressing a receptor specific to the bio-signal transmitter to be detected may be any cell having an ion channel controlled by the bio-signal transmitter that acts on the channel as a ligand, and is preferably originated from any animal having the same neurotransmission mechanism as the detected sample. For example, in the case of detecting a mammalian bio-signal transmitter, the host cell may be selected from the group consisting of a HEK cell, a CHO cell, a COS cell, an NG108 cell, a PC12 cell, and the like.

The present invention has an advantage of directly using a highly sensitive receptor that actually acts on a living body as a sensor, by using a cell from a live organism, not a solid substrate, as a biosensor.

If the bio-signal transmitter to be detected is present in the sample, it reacts with the corresponding receptor expressed on the transfected cell used as a biosensor, thereby opening an ion channel controlled by the receptor, causing an intracellular current change. Therefore, the presence and the concentration of the bio-signal transmitter to be detected can be detected in real-time by measuring the intracellular current. Furthermore, since the current is very sensitive to a merely minute concentration of some materials, the current-based detection can achieve a nanomolar detection limit and millisecond resolution, thereby providing a very accurate analysis.

In an embodiment of the present invention, the transfected cell may express a non-desensitized receptor together with fluorescent materials, making it possible to more easily confirm whether or not the receptor specific to the bio-signal transmitter to be detected is expressed, thereby facilitating the bio-signal transmitter detection. In other words, in order to confirm that the detected intracellular current change is caused by the bio-signal transmitter to be detected, it is important to confirm whether the receptor that serves as a passage of the bio-signal transmitter is expressed or not, which can be more easily confirmed by co-expressing the receptor together with a fluorescent material labeling the receptor. For example, to easily confirm the expression of the bio-signal transmitter specific receptor, the receptor may be co-expressed together with a green fluorescent protein (GFP), dsRed, a red fluorescent protein (RFP), a yellow fluorescent protein (YFP), a cyan fluorescent protein (CFP), or mCherry.

In a preferable embodiment, the biosensor may be a glutamate detecting biosensor including a transfected HEK cell expressing a non-desensitized GluR1(L497Y) and GFP (GluR1(L497Y)/GFP transfected cell, Accession Number: NM_031608).

The transfection method is unlimitedly any method known to the relevant art.

In another aspect, the present invention provides a bio-signal transmitter detector including a transfected cell expressing a receptor specific to the bio-signal transmitter to be detected and an ion channel regulated by the receptor; an electrode; and a current detector.

The current detector may be a patch clamp amplifier.

In still another aspect, the present invention provides a method of detecting a bio-signal transmitter including the steps of:

preparing transfected cells expressing a receptor specific to the bio-signal transmitter to be detected and an ion channel regulated by the receptor;

culturing cells isolated from a sample to be detected to prepare a cell monolayer;

plating and co-culturing the transfected cells on the cell monolayer; and measuring current change in the co-cultured transfected cells through an electrode attached to cells, to detect the presence or concentration of the bio-signal transmitter in real time.

The step of measuring current change may be performed by a sniffer-patch method, and the sniffer-patch method may be performed using a patch clamp amplifier.

As described above, according to the present invention, if the bio-signal transmitter to be detected is present in the sample, it reacts with the corresponding receptor expressed on the transfected cell used as a biosensor, thereby opening an ion channel controlled by the receptor, causing an intracellular current change. Therefore, the presence and the concentration of the bio-signal transmitter to be detected can be detected in real-time by measuring the intracellular current. Furthermore, since the current is very sensitive to a merely minute concentration of some materials, the current-based detection can achieve a nanomolar detection limit and millisecond resolution, thereby providing a very accurate analysis.

The transfected cell used for the detector or the detecting method for a bio-signal transmitter may express a receptor specific to the bio-signal transmitter to be detected together with a fluorescent material. In this case, the detector or the detecting method may further include a conventional fluorescence detector or detecting step.

In the detector or the detecting method for a bio-signal transmitter, the bio-signal transmitter, the receptor, and the transfected cell may be defined as above.

The sample to be detected may be any tissue or cell isolated from a mammal including humans, rodents, and the like, for example, a neuron or a astrocyte from nervous tissue, or a secretory cell secreting hormone.

The biosensor, the detector, and the detecting method according to the present invention may be carried out by a sniffer-patch method as described in "T. G. J. Allen, Trends Neurosci., Vol. 20, No. 5 pp. 192-107, 1997" (the entire contents of which are incorporated herein by reference).

According to the present invention, real-time and nanomolar level detection for a bio-signal transmitter can be achieved by measuring intracellular current change, whereby very sensitive and accurate detection can be achieved. In addition, the present invention allows a millisecond time resolution in micromolar level detection. For example, in micromolar level detection for a bio-signal transmitter, time resolution ranging from 100 microseconds to 1 millisecond can be achievable.

The present invention has an advantage of allowing an accurate and efficient real-time detection of bio-signal transmitter(s) such as hormones, neurotransmitters, and the like that are present in cells in a very small amount, by using a transfected cell that expresses a receptor specific to the bio-signal transmitter to be detected and a ion channel regulated by the receptor as a biosensor, and measuring current induced in the cell.

The present invention is further explained in more detail with reference to the following examples. These examples, however, should not be interpreted as limiting the scope of the present invention in any manner.

EXAMPLES

Example I

Measurement of Glutamate Release

Example 1

Preparation of GluR1(L497Y) Transfected HEK 293 Cells

HEK 293 cells (ATCC1573) were plated onto 12 mm glass coverslips coated with 5-10 ug/ml poly-D-lysine and grown in DMEM media (Gibco, cat# 11960-044) supplemented with 25 mM glucose, 10% heat-inactivated horse serum, and 10% heat-inactivated fetal bovine serum, 2 mM glutamine, and 1000 units/ml penicillin-streptomycin (Banke & Traynelis, 2000; Traynelis & Wahl, 1996). The obtained cultures were maintained at 37° C. in a humidified 5% $CO_2$-containing atmosphere.

HEK 293 cells were transfected with a 1:3.5 ratio of GFP and GluR1(L497Y) using the calcium phosphate method using effectence for 6-8 hours, after which the media was replaced and supplemented with 1 mM kynurenic acid and 10 µM N-(4-hydroxyphenylpropanoyl) spermine or 10 µM CNQX. The transfected HEK cells were subsequently trypsinized and replated onto astrocyte feeder layers derived from either wild-type or PAR1−/− mice 24 hours post-transfection, and recordings were performed 24 hours after replating. The prepared transfectant was used as a biosensor in the following examples.

Example 2

Measurement of Glutamate Release

In this experimental example, the glutamate release from astrocytes was quantitatively evaluated in real time by a "sniffer-patch" detection system. In the system, HEK 293 cells transfected with the non-desensitizing GluR1 mutant L497Y (Stern-Bach et al., 1998), which was prepared in Example 1, were used as a biosensor of glutamate release from cultured cortical astrocytes (in FIG. 1a). The "sniffer-patch" method was performed according to "T. G. J. Allen, Trends Neurosci., Vol. 20, No. 5 pp. 192-107, 1997", unless there is different mention thereto.

2.1: Preparation of Astrocyte Culture

Cultured astrocytes were prepared from P0-P3 postnatal mice obtained from KIST SPF. The cerebral cortex was dissected free of adherent meninges, minced, and dissociated into single cell suspension by trituration through a Pasteur pipette. All procedures involving the use of animals were reviewed and approved by the Emory University IACUC. Dissociated cells were plated onto either 12 mm glass coverslips or 6 well plates coated with 0.1 mg/ml poly-D-lysine. Cells were grown in DMEM media (Gibco, cat# 11960-044) supplemented with 25 mM glucose, 10% heat-inactivated horse serum, and 10% heat-inactivated fetal bovine serum, 2 mM glutamine, and 1000 units/ml penicillin-streptomycin. Cultures were maintained at 37° C. in a humidified 5% $CO_2$-containing atmosphere. Astrocyte cultures prepared in this way were previously determined by GFAP (glial fibrillary acidic protein) staining to be greater than 95% astrocytes (Nicole et al., 2005). In some experiments, the culture media was replaced 24 hours after plating with DMEM with all added components except glutamine, and cultures were maintained for 4 days before experimentation in glutamine-free media.

2.2: Measurement of Glutamate Release from Astrocytes

In the system, HEK 293 cells transfected with the non-desensitizing GluR1 mutant L497Y (Stern-Bach et al., 1998), which was prepared in Example 1, were used as a biosensor of glutamate release from cultured cortical astrocytes. GluR1 (L497Y) responds to glutamate with a sustained current that will temporally follow the glutamate concentration. Thus, this technique provides millisecond time resolution for the detection of micromolar levels of glutamate released from astrocytes.

Figure 1A:
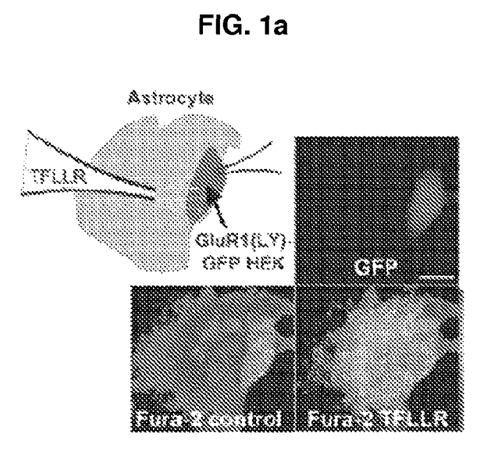
FIG. 1a is a schematic illustrating experimental setup and a GFP fluorescent image of an astrocyte—GluR1(L497Y)/GFP transfected HEK cell co-culture (upper left panel), and ratio images depending on pressure-applied TFLLR (lower left and right panels)
Figure 1B:
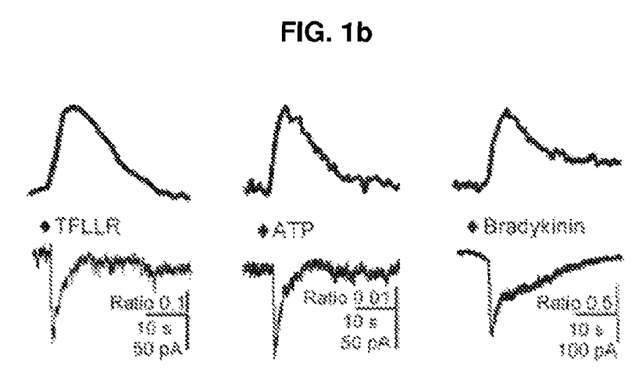
FIG. 1b shows results of quantification of the fluorescence increase in response to brief (<1 sec) pressure application of TFLLR, ATP, and bradykinin in wild-type astrocytes (upper trace), and the inward current induced in adjacent GluR1(L497Y)-transfected HEK cells (lower trace)

GluR1(L497Y)-transfected HEK cells were directly plated onto an astrocyte monolayer, and subsequently the whole cell HEK current response under voltage clamp during brief 0.2 sec application of the PAR1 activator TFLLR (500 μM), ATP (300 μM), or bradykinin (180 μM), respectively, from a pressurized pipette was recorded (FIGS. 1a, and 1b). FIGS. 1a and 1b show the use of GluR1(L497Y) transfected HEK cells as biosensors for astrocytic glutamate release and the measured results thereby.

FIG. 1a is a schematic illustrating experimental setup and a GFP fluorescent image of astrocyte—GluR1(L497Y)/GFP transfected HEK cell co-culture (upper left panel). The lower panel shows the ratio image (510 nm emission; 340 nm/380 nm excitation) of Fura2-AM loaded co-cultures (Example 2.1) before and after brief (<1 sec) pressure-applied TFLLR (500 μM in pipette). The Fura2-AM loading was performed by incubating with 5 μM Fura2-AM in 1 μM pluronic acid (Molecular Probes) for 30 min at room temperature. The calibration bar is 20 μm.

FIG. 1b shows the results of the quantification of the fluorescence increase in response to brief (<1 sec) pressure application of 500 μM TFLLR, 300 μM ATP, and 180 μM bradykinin in wild-type astrocytes (upper trace) recorded together with the inward current induced in adjacent GluR1(L497Y)-transfected HEK cells (lower trace). $Ca^{2+}$ sensitive dye Fura-2-AM recordings revealed that TFLLR, ATP, and bradykinin all increased astrocytic intracellular $Ca^{2+}$ and elicited an inward current in HEK cells expressing GluR1(L497Y).

Figure 1C:
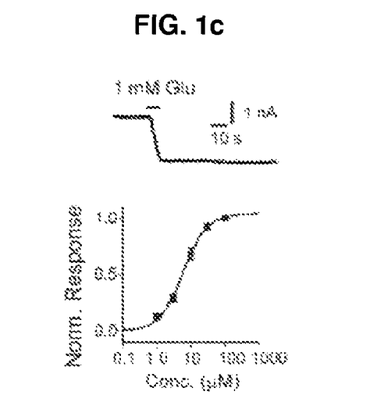
FIG. 1c shows the dose response relationship and current response to pressure application of TFLLR converted to concentration using the dose response relationship and maximal current response of the GluR1(L497Y) transfected HEK cell, and FIG. 1d summarizes the glutamate evoked current response (%) and the peak concentration in GluR1(L497Y) transfected HEK cells to TFLLR application to wild-type and PAR1−/− astrocytes.

FIG. 1c shows the dose response relationship and current response to pressure application of TFLLR converted to concentration using the dose response relationship and maximal current response of the GluR1(L497Y) transfected HEK cell as described in the following Formula 1:

$$\text{Concentration }(t) = EC_{50}[\text{response}(t)/(100-\text{response}(t))]^{(1/n)} \quad \text{(Formula 1)}$$

(where response(t) is the response amplitude expressed as a percent of the maximum achievable response and n is the Hill slope.)

As evaluated by the above formula, $EC_{50}$ value for glutamate activation of GluR1(L497Y) in transfected HEK cells was 6.1 μM (Hill slope 1.3).

Figure 1D:
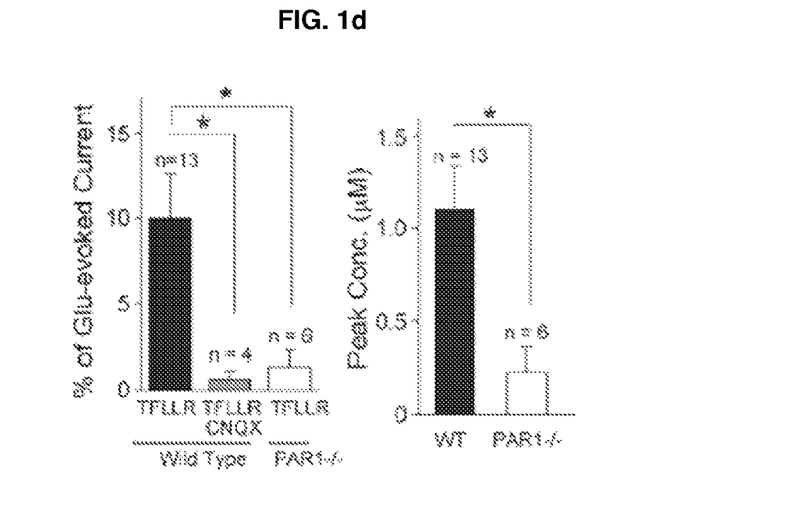

FIG. 1d summarizes the glutamate evoked current response (%) and the peak concentration in GluR1(L497Y) transfected HEK cells to TFLLR application to wild-type and PAR1−/− astrocytes. The glutamate evoked current (%) was 10±2.6% (n=13) when TFLLR was applied to wild-type; 0.64±0.47% when TFLLR+CNQX was applied to wild-type; and 1.4±0.9% when TFLLR was applied to PAR1−/−, *p<0.05, one-way ANOVA), and the maximum concentration was 1.1±0.24 μM and 0.23±0.13 μM in wild-type and PAR1−/− astrocyte cultures, respectively. *p<0.05, unpaired t-test.

As shown in FIG. 1d, from simultaneous imaging of $Ca^{2+}$-sensitive fluorescent dyes, it was confirmed that TFLLR did not alter PAR1−/− astrocytic intracellular $Ca^{2+}$ but did increase HEK cell intracellular $Ca^{2+}$, as expected given endogenous expression of PAR1 in HEK cells. These control experiments were performed on the same day as TFLLR stimulation of HEK cells on wild-type astrocytes, and confirm that PAR1 activators had no direct effect on GluR1 (L497Y) currents in HEK cells.

2.3: Effect of Glutamate in Culture Media of Astrocytes

This experiment was performed using the above sniffer-patch detection system to verify that the astrocytic release of glutamate observed did not reflect a culture artifact.

Figure 4A:
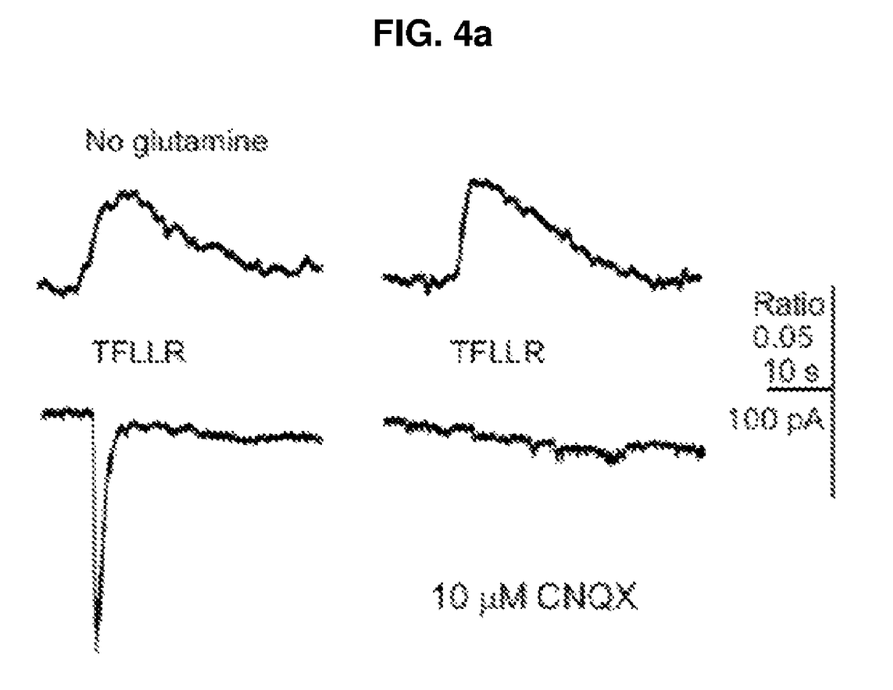
FIG. 4a shows representative traces of a TFLLR-induced fluorescence increase in wild-type astrocytes (upper trace) recorded together with the inward current from GluR1 (L497Y) transfected HEK cell (lower trace), which are co-cultured in a glutamine-free medium.
Figure 4B:
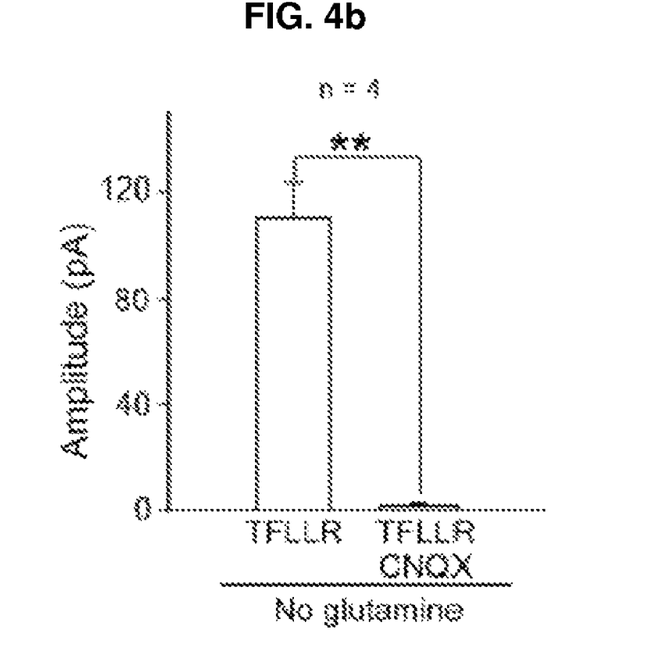
FIG. 4b shows the amplitude changes by TFLLR and CNQX in the glutamine-free medium.

First, cultures were prepared in the absence of glutamine, which should prevent artifactual elevation of intracellular glutamate concentration that might have skewed levels of glutamate release observed. The TFLLR-induced glutamate release in glutamine-free culture media was shown in FIGS. 4a and 4b. FIG. 4a shows representative traces of TFLLR-induced fluorescence increase in wild-type astrocytes (upper trace) recorded together with the inward current from GluR1 (L497Y) transfected HEK cells (lower trace), which are co-cultured in glutamine-free medium. FIG. 4b is a summary of the amplitude changes by TFLLR (500 μM) and CNQX (10 μM) in glutamine-free medium; **p<0.01, paired t-test.

As shown in FIGS. 4a and 4b, TFLLR induced a current response that was 9.7+1.3% (n=4) of the maximal response from astrocytes cultured in the absence of glutamine, which was not significantly different than 10±2.6% (n=13; p>0.05) in the presence of glutamine. In addition, CNQX completely abolished the inward currents evoked by TFLLR, indicating that TFLLR application evoked identical CNQX-sensitive responses in GluR1(L497Y) transfected HEK cells when astrocytes were cultured in glutamine-free media. These results suggest that TFLLR-induced glutamate release was not solely the result of potentially high intracellular glutamate that might arise in glutamine-supplemented culture media.

Example 3

Glutamate Release from Astrocytes in Hippocampal Slices

Cells were acutely dissociated from the CA1 region of hippocampal slices prepared from transgenic mice (Jackson Laboratories) expressing GFP under control of the GFAP promoter (Brenner et al., 1994), allowing to unambiguously identify isolated hippocampal astrocytes that had not been subject to tissue culture. Cells were dissociated directly onto GluR1(L497Y)-transfected HEK cells obtained in Example 1. Subsequently GFP-expressing astrocytes that came to rest adjacent to a GluR1(L497Y)-transfected HEK cell were identified, and patch clamp recordings from the GluR1(L497Y)-transfected HEK cell was used to detect glutamate release from the astrocyte.

Figure 2A:
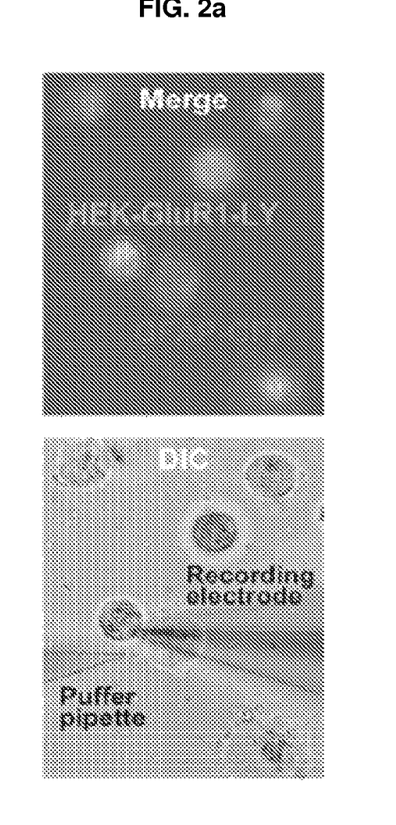
FIG. 2a shows images of GFAP-GFP labeled astrocytes (green) plated onto GluR1(L497Y) transfected HEK cells (red) (upper panel), and a DIC image of the recording electrode and pressurized agonist filled pipette in the co-culture (lower panel)
Figure 2B:
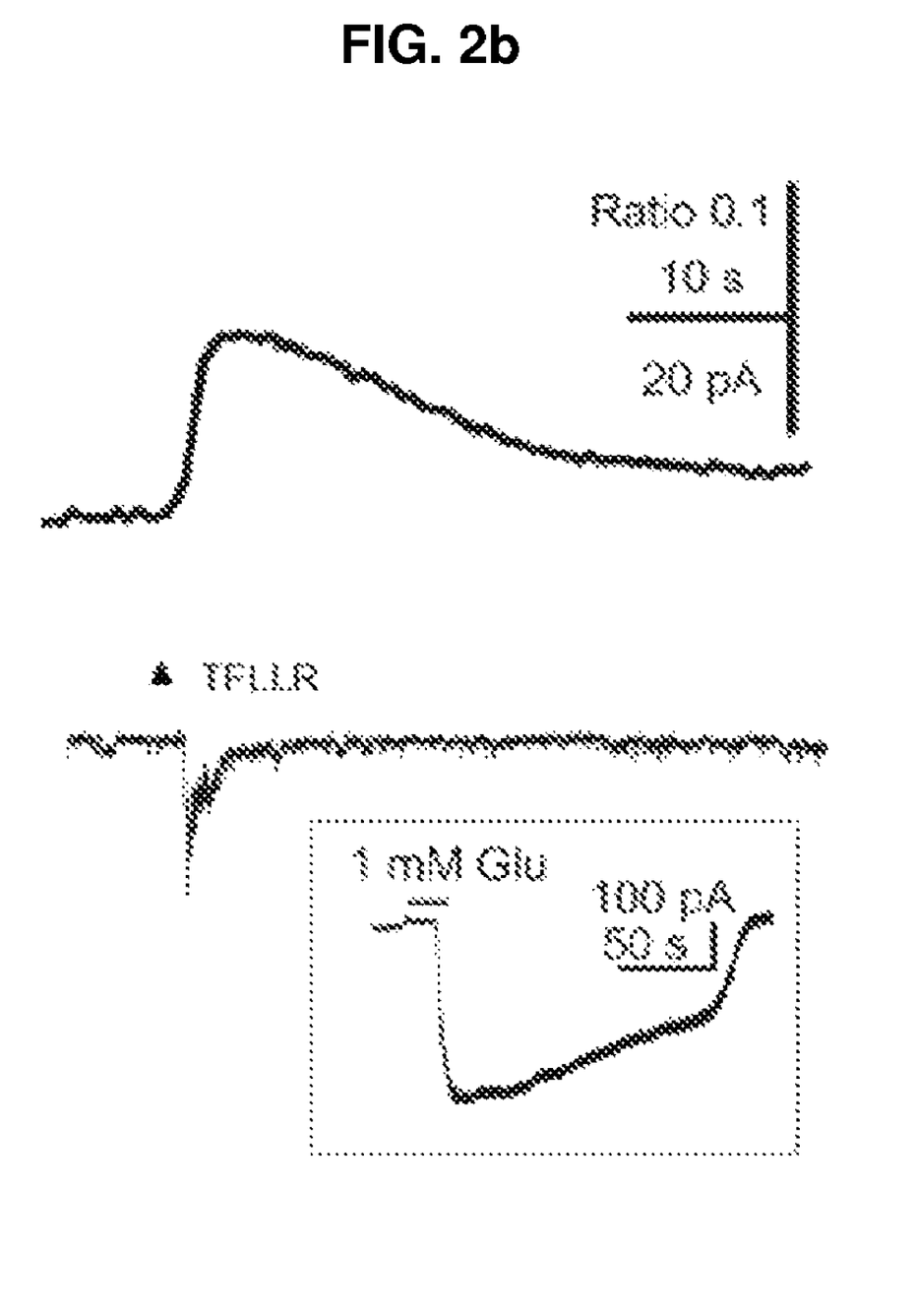
FIG. 2b shows representative traces of Fura-2 fluorescence increase in GFAP-GFP labeled astrocyte (upper trace), the inward current from GluR1(L497Y) transfected HEK cell (lower trace), and the response to 10 sec application of a maximally effective concentration of glutamate on the same cell (insert).

TFLLR-evoked glutamate release from acutely dissociated CA1 astrocytes is shown in FIGS. 2a and 2b. In FIG. 2a, the upper panel shows the images of acutely dissociated GFAP-GFP labeled astrocytes (green) plated onto GluR1(L497Y) transfected HEK cells (red), and the lower panel shows a DIC image of the recording electrode and pressurized agonist filled pipette in the same co-culture as above. FIG. 2b shows representative traces of Fura-2 fluorescence increase in GFAP-GFP labeled astrocytes (upper trace) recorded together with the inward current from GluR1(L497Y) transfected HEK cells (lower trace) in response to brief (1 sec) application of TFLLR. The inset shows the response to 10 sec application of a maximally effective concentration of glutamate (1 mM) on the same cell.

FIGS. 2a and 2b show the results from a representative experiment in which brief application of the selective PAR1 activator TFLLR from a pressurized pipette evoked a response in nearby GluR1(L497Y)-transfected HEK cells. Similar results were found in 4 cells (1.46+0.54 μM; n=4), which confirms that glutamate release may occur from astrocytes in slices.

Example 4

Comparison of Glutamate Release in Neurons and Astrocytes

Figure 3:
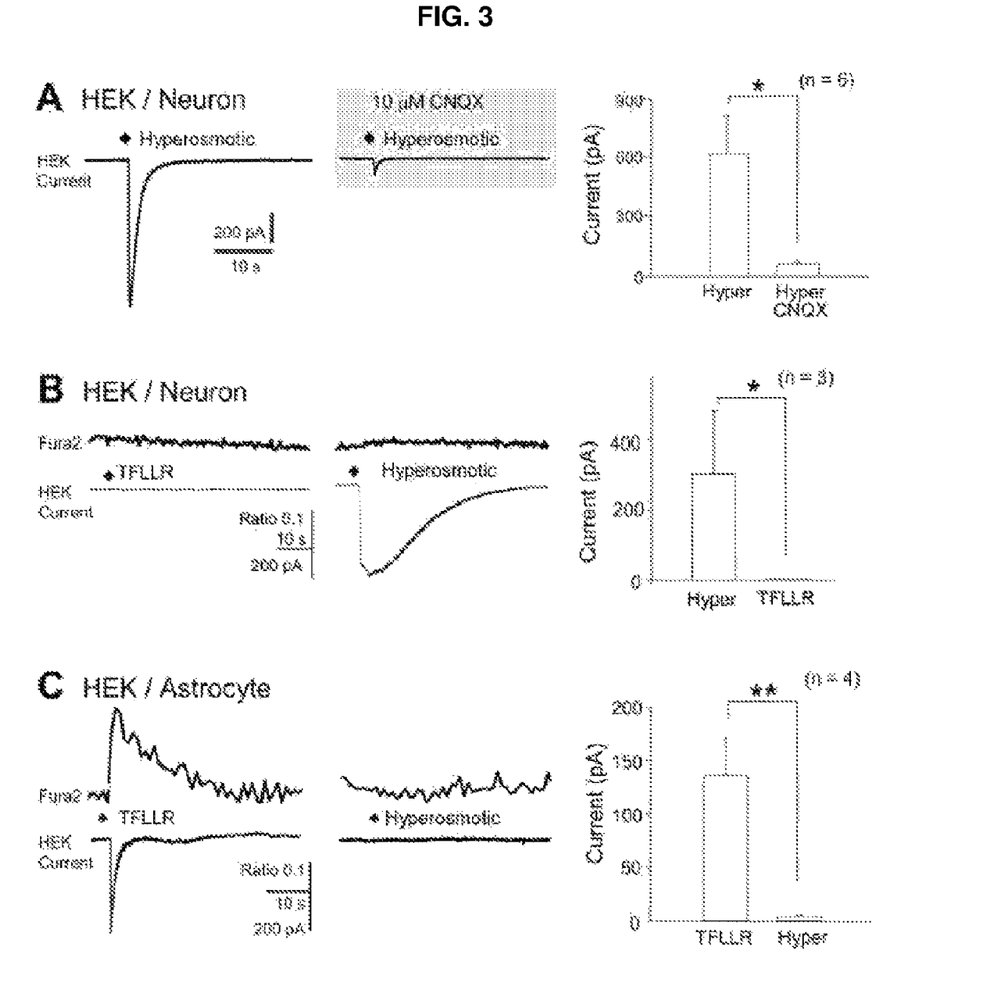
FIG. 3 shows the glutamate release from neurons measured using GluR1(L497Y)-transfected HEK cells (a), the glutamate-induced current amplitude change (b), and the response to application of a maximally effective concentration of glutamate on GluR1(L497Y)-transfected HEK cells (c).

Because PAR1 activators induce little or no intracellular $Ca^{2+}$ signaling in CA1 pyramidal cells or acutely dissociated CA1 neurons, it may be predicted that PAR1 activators will not induce glutamate release from neurons. To verify this prediction, effects of a hyperosmotic solution on the glutamate-release from cultured neurons and astrocytes were evaluated and are shown in FIGS. 3a to 3c.

FIG. 3a shows the ability of a GluR1(L497Y)-transfected HEK co-culture system to detect CNQX-sensitive glutamate release from neurons in response to hyperosmotic solutions (530 mOsm, n=6), which stimulate vesicular release of glutamate from cultured central neurons. The left panel shows the detection results of neuronal glutamate release by using a hyperosmotic solution (530 mosmol, H.O.) and GluR1(L497Y)-transfected HEK cell. The detection is abolished by the treatment of 10 μM CNQX. The right panel is the summary of the current amplitude changes; *p<0.05; paired t-test (n=6).

FIG. 3b shows that HEK cells expressing GluR1(L497Y) may detect the neuronal glutamate upon the treatment of the hyperosmotic solution (301.6±179.3 pA, n=3), however it shows no response to application of 30 μM TFLLR (3.0±0.1 pA, n=3). *p<0.05; paired t-test. That is, a brief application of TFLLR caused no detectable glutamate-induced current in GluR1(L497Y)-transfected HEK cells adjacent to neurons.

FIG. 3c shows the results of same-day glutamate responses to activation of PAR1 in astrocytes, as a positive control for TFLLR activation of PAR1, wherein HEK cells expressing GluR1(L497Y) may detect the astrocytic glutamate release from astrocytes during application of TFLLR (136±35 pA, n=4), however it shows virtually no response to application of the hyperosmotic solution (4.8±1.4 pA, n=4). **p<0.01; unpaired t-test.

Example II

Measurement of D-serine or Glycine Release

Example 5

Preparation of Transfected HEK 293 Cells Expressing NMDA Receptor

HEK 293 cells (ATCC1573) were plated onto 12 mm glass coverslips coated with 5-10 ug/ml poly-D-lysine and grown in DMEM media (Gibco, cat# 11960-044) supplemented with 25 mM glucose, 10% heat-inactivated horse serum, and 10% heat-inactivated fetal bovine serum, 2 mM glutamine, and 1000 units/ml penicillin-streptomycin (Banke & Traynelis, 2000; Traynelis & Wahl, 1996). The obtained cultures were maintained at 37° C. in a humidified 5% $CO_2$-containing atmosphere.

HEK 293 cells were transfected NR1-1a and NR2A2D at a ratio of 1:2 by using the calcium phosphate method using effectence for 6-8 hours, after which the media was replaced and supplemented with 5 mM magnesium chloride and 10 μM D-2-amino-phosphonopentanoic acid or 10 μM D-AP5. The transfected HEK cells were subsequently trypsinized and replated onto astrocyte feeder layers derived from wild-type 24 hours post-transfection, and recordings performed 24 hours after replating. The prepared transfectant was used as a biosensor in the following examples.

Example 6

Measurement of D-serine or Glycine Release

The amount of D-serine or glycine release was measured by the same method as in Example 2, except for using the transfected HEK 293 cells prepared in Example 5 as a biosensor, 500 uM TFLLR, and media containing 100 uM glutamate or 100 uM glutamate+10 uM DCKA (5,7-dichlorokynurenic acid).

The NMDA receptor has two subunits of a glutamate binding subunit and a D-serine or glycine binding subunit. To activate the NMDA receptor, it is necessary for the two subunits to bind to the corresponding binding materials, respectively. The activation may be confirmed by measuring intracellular inward current.

In this example, the media was supplemented with sufficient glutamate to saturate the glutamate domain. The intracellular inward current in the biosensor prepared in Example 5, under the conditions with or without treating a glycine binding domain blocker, DCKA, which artificially makes a glycine-free or D-serine-free condition, to examine the glycine or D-serine detecting ability of the biosensor.

Figure 5A:
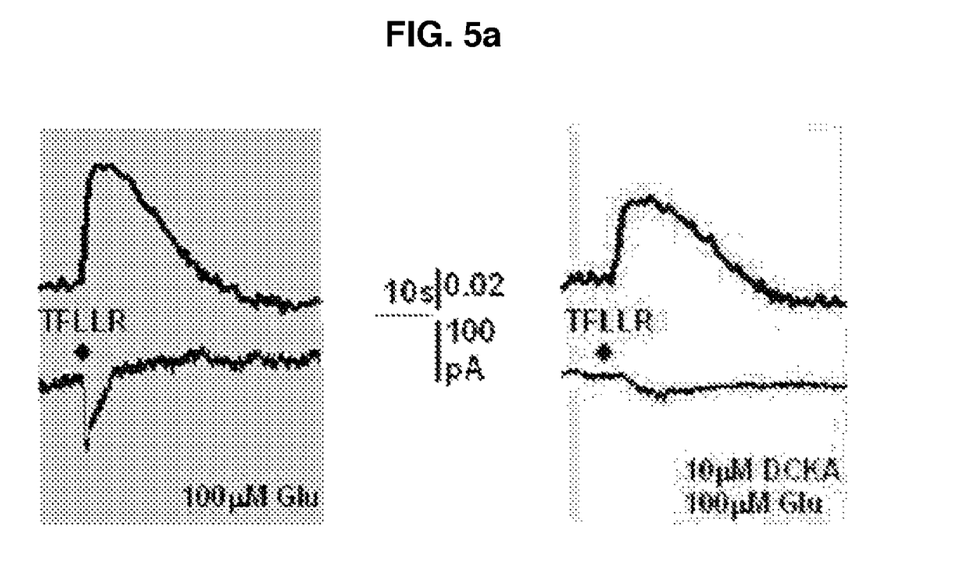
Figure 5B:
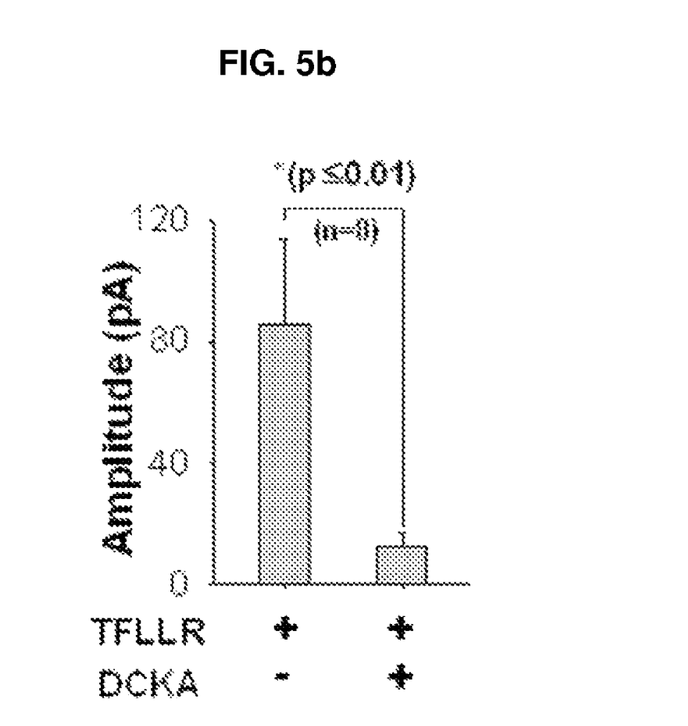

The obtained detection results are shown in FIGS. 5a and 5b. FIG. 5a shows the cases in which glutamate and DCKA are all treated (right panel), and in which only glutamate is treated (left panel), wherein in each case, the upper trace represents the calcium increment recorded from astrocytes and the lower trace shows the inward current recorded from HEK293 cells; and 5b is a bar graph for summary of current traces of left and right panels of 5a. As is known from the comparison of both panels of FIG. 5a, the inward current value after treating TFLLR is considerably decreased in the case with DCKA treatment (right panel) compared with the case without DCKA treatment (left panel), indicating that the biosensor according to the present invention is capable of detecting D-serine or glycine with high sensitivity.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method of detecting a bio-signal transmitter comprising the steps of:
   preparing transfected cells expressing a receptor specific to the bio-signal transmitter to be detected and an ion channel regulated by the receptor;
   culturing cells isolated from a sample to prepare a cell monolayer;
   plating and co-culturing the transfected cells on the cell monolayer; and
   measuring current change in the co-cultured transfected cells through an electrode attached to cells, to detect the presence of the bio-signal transmitter from the cultured cells from the sample in real time,
   wherein the receptor is GluR1, GluR1LY, GluR2, GluR3, GluR4, GluR5, GluR6, GluR7, or mGluR1-7 and the bio-signal transmitter is glutamate, or the receptor is NR1-1a/NR2A2D and the bio-signal transmitter is D-serine or glycine.

2. The method according to claim 1, wherein the transfected cell is prepared from a host cell selected from the group consisting of a HEK cell, a CHO cell, a COS cell, an NG108 cell, and a PC12 cell.

3. The method according to claim 1, wherein the transfected cell further expresses a fluorescent protein together with the receptor specific to the bio-signal transmitter, wherein the fluorescent protein is selected from the group consisting of a green fluorescent protein (GFP), dsRed, a red fluorescent protein (RFP), a yellow fluorescent protein (YFP), a cyan fluorescent protein CFP and mCherry 4. The method according to claim 1, wherein the step of measuring current change is performed by a sniffer-patch method where a membrane patch is excised from the transfected cell and said patch is voltage-clamped in an outside-out configuration to a potential in a range capable of providing an impulse sufficient for ion transfer through the channel to be detected while preventing activation of voltage-gated ion channels.

5. The method according to claim 4, wherein the sniffer-patch method is performed by using a patch clamp amplifier.

* * * * *